(12) United States Patent
Kondo et al.

(10) Patent No.: US 10,564,035 B2
(45) Date of Patent: Feb. 18, 2020

(54) DEVICE AND METHOD FOR SPECTRUM DETERMINATION

(71) Applicant: JASCO Corporation, Tokyo (JP)

(72) Inventors: Yoshiro Kondo, Tokyo (JP); Koshi Nagamori, Tokyo (JP)

(73) Assignee: JASCO Corporation, Tokyo (JP)

( * ) Notice: Subject to any disclaimer, the term of this patent is extended or adjusted under 35 U.S.C. 154(b) by 0 days.

(21) Appl. No.: 15/968,307

(22) Filed: May 1, 2018

(65) Prior Publication Data

US 2018/0321086 A1   Nov. 8, 2018

(30) Foreign Application Priority Data

May 8, 2017   (JP) ................. 2017-092438

(51) Int. Cl.

| | | |
|---|---|---|
| *G01J 3/44* | (2006.01) | |
| *G01J 3/28* | (2006.01) | |
| *G01N 21/64* | (2006.01) | |
| *G01N 21/27* | (2006.01) | |
| *G01N 21/19* | (2006.01) | |
| *G01J 3/12* | (2006.01) | |
| *G01J 3/02* | (2006.01) | |
| *G01J 3/42* | (2006.01) | |

(52) U.S. Cl.
CPC ............. *G01J 3/28* (2013.01); *G01J 3/0224* (2013.01); *G01J 3/12* (2013.01); *G01J 3/42* (2013.01); *G01N 21/19* (2013.01); *G01N 21/27* (2013.01); *G01N 21/64* (2013.01)

(58) Field of Classification Search
CPC .... G01J 3/28; G01J 3/12; G01J 3/0224; G01J 3/42; G01N 21/19; G01N 21/27; G01N 21/64; G01M 13/04; G01H 17/00
See application file for complete search history.

(56) References Cited

U.S. PATENT DOCUMENTS

2014/0009751 A1* 1/2014 Pezzaniti ........... G01N 33/2835
356/70

FOREIGN PATENT DOCUMENTS

JP   H06160188 A   6/1994

* cited by examiner

*Primary Examiner* — Abdullahi Nur
(74) *Attorney, Agent, or Firm* — Rankin, Hill & Clark LLP (57) ABSTRACT

The present invention relates to improvement in accuracy in a device and a method for determining whether a spectrum of a target sample coincide with a standard spectrum or not. A spectrum determination device 10 determines whether a sample spectrum coincides with a reference spectrum or not by the reference spectrum obtained from a spectrum group. The spectrum determination device 10 comprises a storage unit 26 for storing the reference spectrum, and a determination unit 28 for comparing the reference spectrum and the sample spectrum to determine a sample 20 from the comparison result. The reference spectrum is set with a differing weighting for each point. The determination unit 28 calculates an individual coincidence with the sample spectrum for each point of the reference spectrum, and calculates a coincidence of the sample spectrum with the reference spectrum by the individual coincidence and the differing weighting to determine the sample 20.

21 Claims, 5 Drawing Sheets

(a) Spectrum group (b) Reference spectrum

FIG.5

DEVICE AND METHOD FOR SPECTRUM DETERMINATION

RELATED APPLICATIONS

This application claims the priority of Japanese Patent Application No. 2017-92438 filed on May 8, 2017, the disclosure of which is incorporated herein by reference in its entirety.

FIELD OF THE INVENTION

The present invention relates to a device and a method for determining a spectrum, and particularly to improvement in accuracy in a device and a method for determining whether a spectrum of a target sample coincides with a standard spectrum or not.

BACKGROUND OF THE INVENTION

Conventionally, various spectrum determination are used in quality control of products in food and pharmaceutical fields. For example, spectrum determination methods such as a method which compares one reference spectrum (standard spectrum) of a known substance stored in a library with one spectrum of a target sample to confirm denaturation of the target sample, and a method which measures the reference spectrum multiple times, takes dispersion thereof into consideration, and compares the reference spectrum and the spectrum of the target sample to consider the statistical difference between the two are known.

Such device and method for determining a spectrum are used in cases where denaturation of protein is confirmed by comparing the intensity and the shape of protein spectrum (by comparing the intensity and the shape of normal protein as a reference and denatured protein).

Although characteristic (and tendency) of a spectrum can be reproduced by measuring the reference spectrum multiple times, an exactly same spectrum cannot be reproduced due to effects of random noises and the like in actual measurement. Therefore, efficient determination was difficult in spectrum determination which uses conventional spectrum measurement, and reliability of determination result was limited. Patent Literature 1 discloses a method for detecting a peak position of an optical spectrum. The method comprises: performing even-order differentiation of the optical spectrum; and weighting the obtained differential spectrum and the original optical spectrum respectively to obtain a mixed spectrum by adding or multiplying the two by corresponding points. Thus, numerous sharp and high (deep) peak positions in the optical spectrum can be efficiently detected at once.

CITATION LIST

Patent Literature

PATENT LITERATURE 1: Japanese Patent Publication No. JPH06-160188

DISCLOSURE OF THE INVENTION

Problem to be Solved by the Invention

As disclosed in Patent Literature 1, numerous peak positions can be detected at once by performing even-order differentiation of the optical spectrum, and weighting the obtained differential spectrum and the original optical spectrum respectively to obtain a mixed spectrum by adding or multiplying the two by corresponding points. However, it is difficult to improve measurement accuracy by this method, because the reference spectrum becomes a specific spectrum that differs in each measurement. Therefore, there is still plenty of room for improvement.

Means to Solve the Problem

The present invention has been made in view of the problems of the prior art, and the object is to provide a device and a method for determining a spectrum that are capable of accurate determination by contriving the reference spectrum upon determining a spectrum for identifying samples and confirming denaturation.

To solve the problems mentioned above, the spectrum determination device according to the present invention compares a reference spectrum prepared from a spectrum group that has been measured multiple times and a sample spectrum to determine whether the sample spectrum coincides with the reference spectrum or not, the device comprising:

a storage unit for storing the reference spectrum, and a determination unit for comparing the reference spectrum and the sample spectrum to determine the sample from a comparison result, wherein the reference spectrum is set with a differing weighting for each point;

the determination unit calculates an individual coincidence with the sample spectrum for each point of the reference spectrum, and calculates a coincidence of the sample spectrum with the reference spectrum by the calculated individual coincidence and the differing weighting to determine the sample.

Further, the spectrum determination device according to the present invention is characterized in that a part where dispersion of the spectrum group is large is lightly weighted, and a part where dispersion of the spectrum group is small is heavily weighted in the reference spectrum.

Further, the spectrum determination device according to the present invention is characterized in that the differing weighting for each point of the reference spectrum is calculated by a standard deviation of dispersion of the spectrum group.

Further, the spectrum determination device according to the present invention is characterized in that the reference spectrum stored in the storage unit is a circular dichroism spectrum, and the determination unit is capable of confirming denaturation of protein by the circular dichroism spectrum.

Further, the spectrum determination method according to the present invention compares a reference spectrum prepared from a spectrum group that has been measured multiple times and a sample spectrum to determine whether the sample spectrum coincides with the reference spectrum or not, the method comprising steps of:

setting a differing weighting for each point of the reference spectrum;

detecting the sample spectrum by spectrum measurement;

calculating an individual coincidence with the sample spectrum for each point of the reference spectrum; and calculating a coincidence of the sample spectrum with the reference spectrum by the individual coincidence and the differing weighting to determine the sample.

Further, the spectrum determination method according to the present invention is characterized in that a part where dispersion of the spectrum group is large is lightly weighted, and a part where dispersion of the spectrum group is small is heavily weighted in the reference spectrum.

Further, the spectrum determination method according to the present invention is characterized in that the differing weighting for each point of the reference spectrum is calculated by a standard deviation of dispersion of the spectrum group.

Further, the spectrum determination method according to the present invention is characterized in that the reference spectrum prepared from the spectrum group is a circular dichroism spectrum.

Further, the spectrum determination method according to the present invention is capable of confirming denaturation of protein by the reference spectrum which is the circular dichroism spectrum.

Further, a program for executing the determination unit according to the present invention is a program which compares the reference spectrum and the sample spectrum to determine whether the sample spectrum coincides with the reference spectrum or not from the comparison result, the program that executes steps of:

setting a differing weighting for each point of the reference spectrum prepared from a spectrum group that has been measured multiple times;

calculating an individual coincidence with the sample spectrum for each point of the reference spectrum; and calculating a coincidence of the sample spectrum with the reference spectrum by the individual coincidence and the differing weighting to determine the sample.

Effect of the Invention

According to the present invention, the spectrum determination device comprises a storage unit for storing a reference spectrum, and a determination unit for determining whether a sample spectrum coincide with the reference spectrum or not. The device sets a differing weighting for each point of the reference spectrum depending on dispersion of a spectrum group, calculates an individual coincidence with the sample spectrum for each point, and calculates a coincidence of the sample spectrum by the individual coincidence and the differing weighting, so that the device can perform a highly accurate determination of the sample. For example, a part where dispersion of the spectrum group is large is lightly weighted, and a part where dispersion of the spectrum group is small is heavily weighted for each point of the reference spectrum, so that the sample can be determined with high accuracy.

BEST MODE FOR CARRYING OUT THE INVENTION

Hereinbelow, the spectrum determination device of the present invention is described with reference to the figures, but is not limited to the examples described below unless the aim of the present invention is not exceeded.

Figure 1:
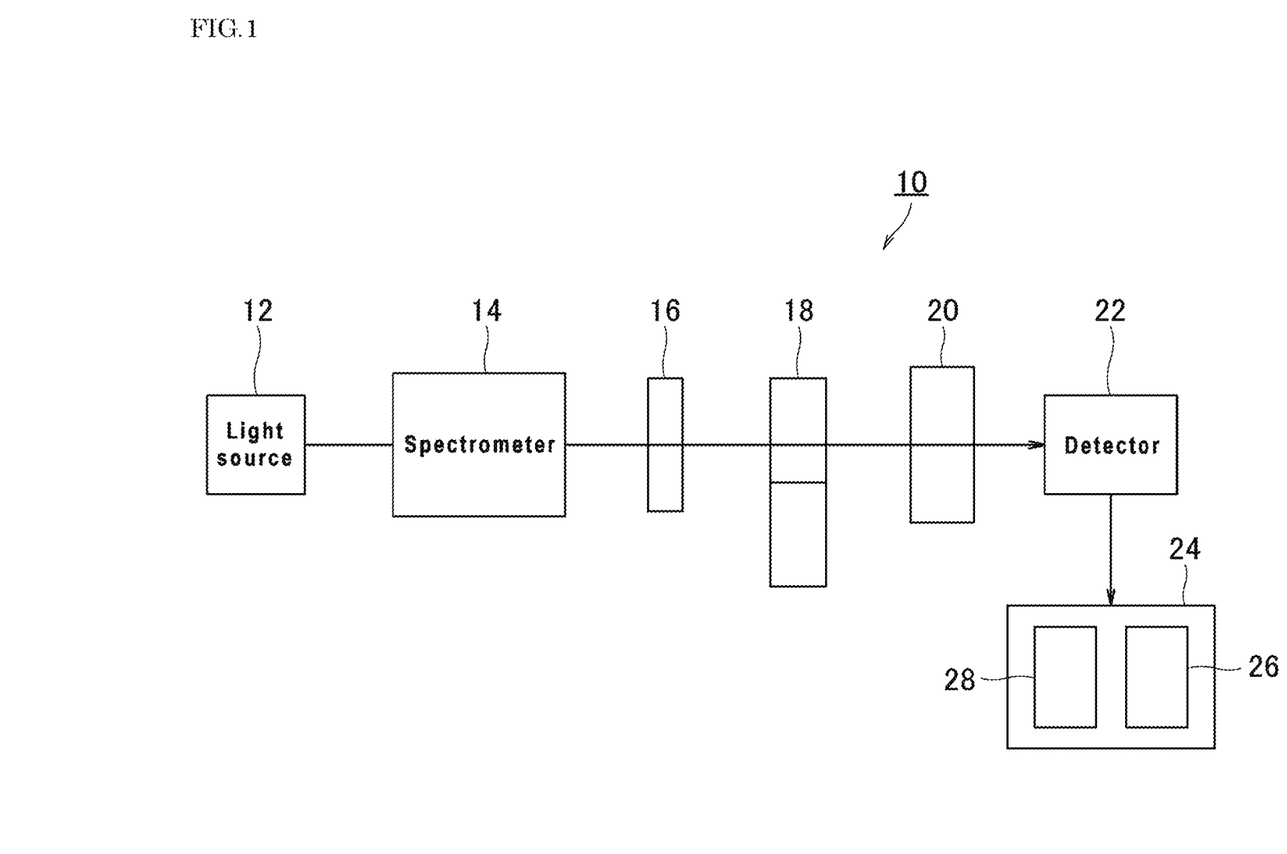
FIG. 1 is a schematic diagram of a spectrum determination device according to an embodiment of the present invention.

FIG. 1 is a schematic diagram of a spectrum determination device according an embodiment of the present invention. The spectrum determination device is integrated with a circular dichroism measurement device that transmits right-handed and left-handed circularly polarized lights through the sample to detect an absorbance difference thereof. To describe necessary processes (reference measurement for obtaining a reference spectrum, spectrum measurement for obtaining a sample spectrum of a sample, and spectrum determination for comparing the reference spectrum and the sample spectrum to determine the sample) for the present embodiment, the spectrum determination device is integrated with a general spectrum measurement device. The spectrum determination device 10 in FIG. 1 comprises a light source 12 for irradiating a measurement light to a sample 20, a spectrometer 14 for spectrally dispersing the measurement light from the light source 12 into a monochromatic light, a polarizer 16 for linearly polarizing the light from the spectrometer 14, a PEM (Photoelastic Modulator) 18 for giving a phase difference to the linearly polarized light from the polarizer 16, the sample 20 as an object to be measured, a detector 22 for detecting the light transmitted through the sample 20, and a determination section (determination device) 24 for comparing the detected light with a known reference spectrum to identify the measured spectrum.

The light irradiated from the light source 12 is spectrally dispersed into a monochromatic light by the spectrometer 14, and linearly polarized by the polarizer 16 to reach the PEM 18. Then, a phase difference is given to the light when it transmits through the PEM 18, and becomes a circularly polarized light that reverses in right-handed and left-handed directions. The right-handed and left-handed circular polarized lights are made incident to the sample 20. The sample 20 has CD (circular dichroism), and when the right-handed and left-handed circularly polarized lights transmit through the sample 20, it is absorbed differently at right side and left side, so that the detector 22 detects the light as the light having intensity fluctuation which depends on CD. The detected light is sent to the determination section 24 as a spectrum of an electric signal for spectrum determination. Specifically, the determination section 24 comprises a storage unit 26 for storing the reference spectrum, and a determination unit 28 for comparing the reference spectrum and the sample spectrum of the sample 20 to determine whether the sample spectrum coincide with the reference spectrum or not. The determination unit 28 identifies the sample 20 and/or confirms denaturation of the same.

<Reference Measurement>

Figure 2:
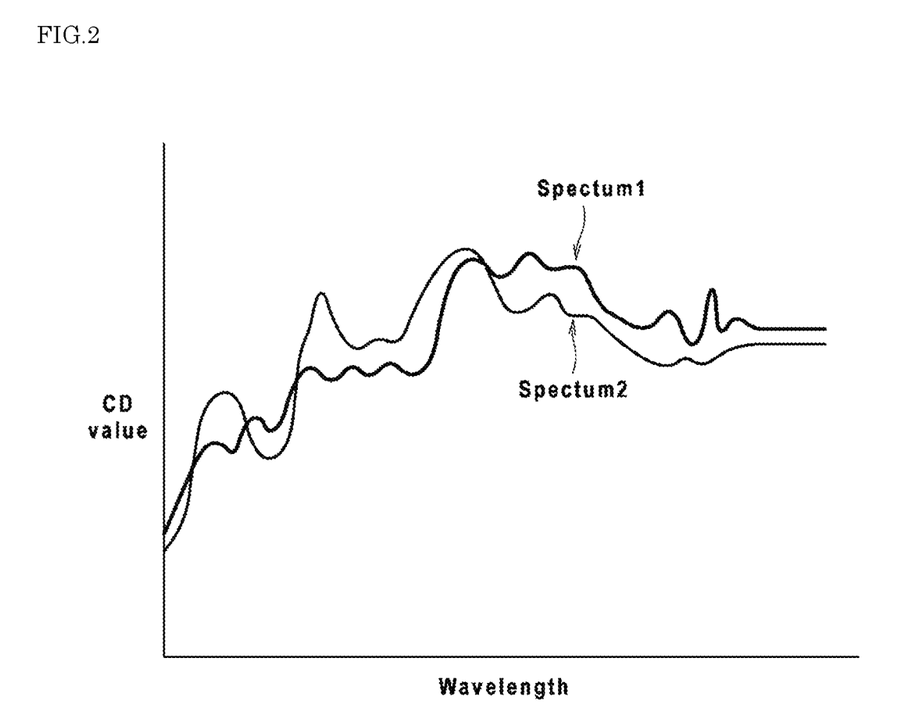
FIG. 2 is a schematic diagram of a spectrum group obtained by reference measurement used in the spectrum determination device according to the embodiment of the present invention.

In the present embodiment, before performing spectrum measurement for obtaining the sample spectrum of the sample 20, the reference spectrum for comparing with the sample spectrum needs to be prepared. Therefore, reference measurement is performed to obtain the reference spectrum at first. FIG. 2 is a schematic diagram of the spectrum group obtained by reference measurement performed by the spectrum determination device 10 according to the present embodiment. In FIG. 2, two spectra (Spectrum 1 and 2) are shown to make the explanation easier. When reference measurement is performed for multiple times to prepare the reference spectrum, the spectrum is measured as a different spectrum in each measurement due to various parameters in most cases although reference measurement is performed under the same condition. As shown in FIG. 2, for example, two spectra are measured under the same condition, but it cannot be said that they are completely identical although characteristic and tendency as a spectrum are equivalent.

That is, when the reference spectrum prepared from one spectrum (for example, Spectrum 1) is used to determine the spectrum of the sample 20, it is difficult to perform determination (identification of the sample 20 and confirmation of denaturation of the same) with good accuracy. Hence, it is preferable to perform reference measurement multiple times in the present embodiment. For example, it is preferable that reference measurement is performed at least 10 times. Further, when shortening of measurement time is considered, it is preferable that reference measurement is performed at least 5 times. Further, when improvement in accuracy is considered, it is preferable that reference measurement is performed at least 20 times. The reference spectrum used for actual spectrum measurement is prepared by the spectrum group measured in such way.

<Reference Spectrum>

Figure 3:
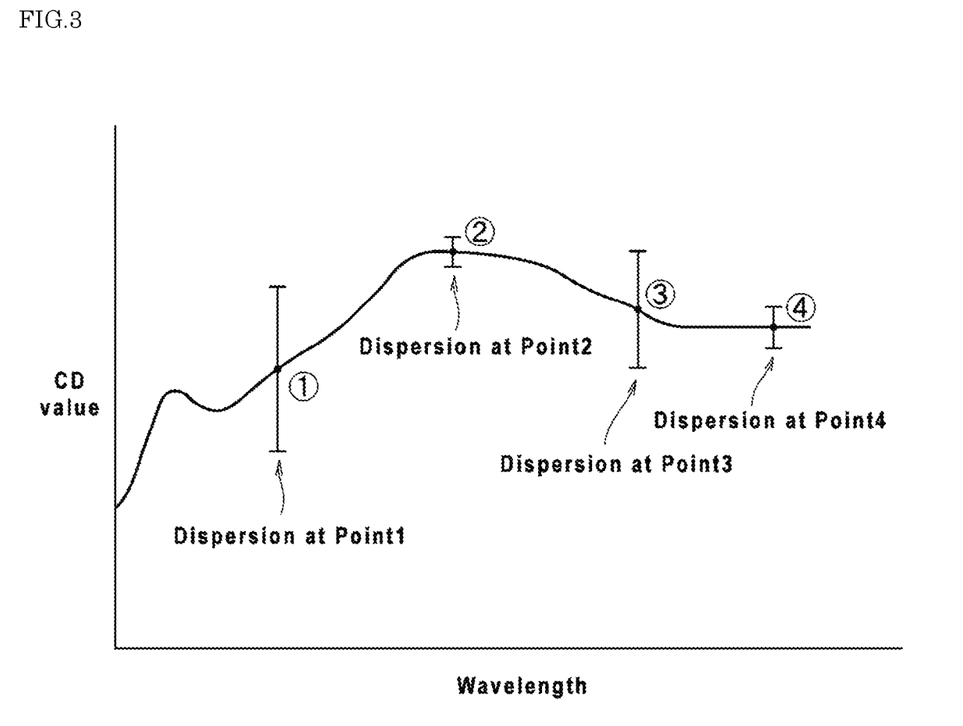
FIG. 3 is a schematic diagram of a reference spectrum according to the embodiment of the present invention.

As described above, the spectrum obtained by reference measurement (Spectrum 1 and 2 in FIG. 2) is used for preparation of the reference spectrum as the spectrum group. FIG. 3 is a schematic diagram of the reference spectrum of the present embodiment. The reference spectrum in FIG. 3 is an average spectrum shown by a solid line as an average value of the spectrum group obtained by reference measurement. Further, the reference spectrum of the present embodiment is set with a weighting that differs for each point of the average spectrum. For example, as shown in FIG. 3, dispersion (dispersion width of the spectrum group) in points 1 to 4 vary respectively, and this dispersion is used to set a weighting that differs for each point.

Figure 4:
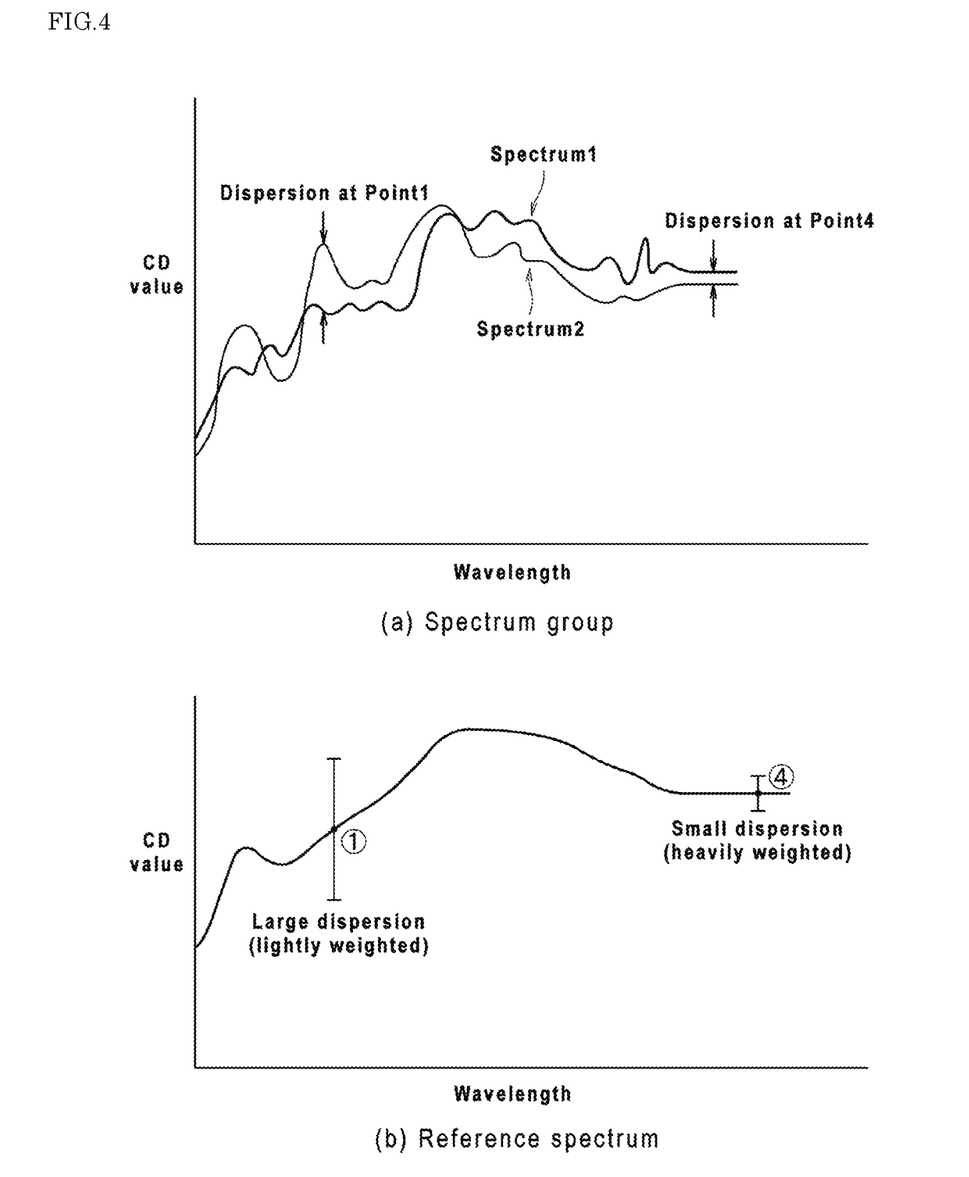
FIG. 4 is a schematic diagram of the spectrum group and the reference spectrum according to the embodiment of the present invention.

The spectrum group shown in FIG. 2 is analyzed under a fixed condition to set the differing weighting for each point. For example, the weighting for measuring the reference spectrum can be set lightly for a part where difference of CD values between the Spectrum 1 and 2 in FIG. 2 is relatively large (a point where dispersion is large), and the weighting for measuring the reference spectrum can be set heavily for a part where difference of CD values between the Spectrum 1 and 2 is small (a point where dispersion is small). Specifically, as shown in FIG. 4 (a), the weighting at Point 1 is set lightly because dispersion of CD values of each spectrum is large, and the weighting at Point 4 is set heavily because dispersion of CD values of spectra is small (FIG. 4 (b)). Accordingly, the weighting for each point of the reference spectrum is set by calculating a gap, dispersion and the like of CD values of the spectrum group.

Further, the weighting for each point of the reference spectrum may be set from known spectrum information, for example. The weighting can be set heavily for a part important for specifying the substance (identification of the sample 20 and confirmation of denaturation of the same), and the weighting can be set lightly for a part of less importance for specifying the substance. Further, the reference spectrum can be preferably prepared by combining dispersion of CD values of the spectrum group and known spectrum information to set the weighting for each point. Practically, with respect to the spectrum group obtained by reference measurement performed for 5 to 20 times or more, for example, the reference spectrum having the average spectrum and differing weightings for each point as described above are prepared. Preparation of the reference spectrum can be performed by the determination unit 28, or a different reference spectrum preparation unit can be provided to the spectrum determination device 10. Then, the prepared reference spectrum is stored in the storage unit 26.

Specifically, the weighting for each point of the reference spectrum can be calculated by: calculating a value of dispersion for each point by a standard deviation, for example, with the spectrum group prepared by reference measurement performed for 5 to 20 times or more, and dividing the score for each point of the reference spectrum by dispersion (standard deviation, and the like). Accordingly, the weighting for a point having a large dispersion can be set lightly, and the weighting for a point having a small dispersion can be set heavily.

Further, a plurality of the spectrum group can be used to calculate the dispersion value σi for each spectrum wavelength by the following model equation.

$$\sigma(\lambda i) = ae^{-\frac{\lambda i - \lambda 0}{a}} + b \qquad \text{[Equation 1]}$$

Further, the dispersion value obtained by the above model equation can be used to calculate a correlation coefficient by the following equation for spectrum determination.

$$I = \frac{\sum_{i=1}^{N}\left\{\frac{(R_i - \overline{R})(U_i - \overline{U})}{\sigma i}\right\}}{\sqrt{\sum_{i=1}^{N}\left\{\frac{(R_i - \overline{R})^2}{\sigma i}\right\}}\sqrt{\sum_{i=1}^{N}\frac{(U_i - \overline{U})^2}{\sigma i}}} \qquad \text{[Equation 2]}$$

N Number of data
Ui: i th data value of an unknown sample
Ri: i th data value of a known sample <Spectrum Determination>

Figure 5:
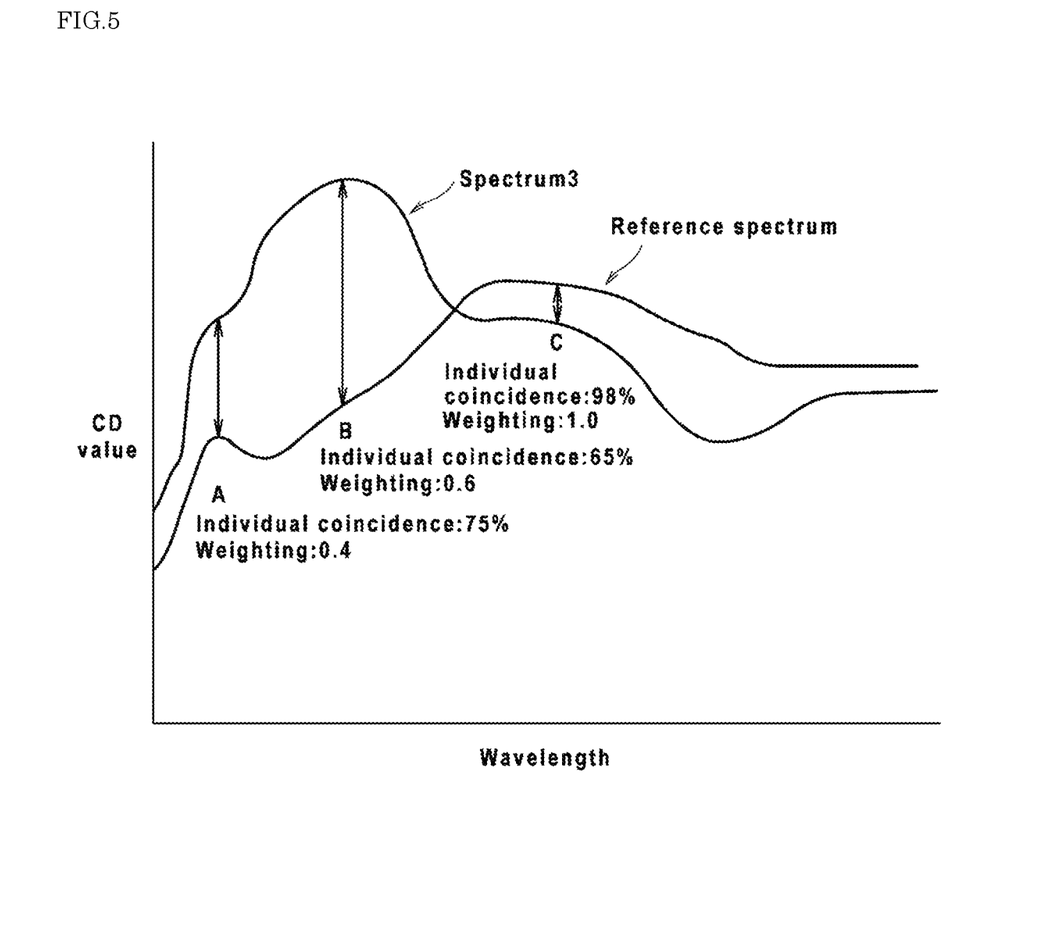
FIG. 5 is a schematic diagram of spectrum determination performed by a spectrum determination device according to the present embodiment.

FIG. 5 is a schematic diagram describing spectrum determination performed by the spectrum determination device (circular dichroism measuring device) 10 according to the present embodiment. Spectrum 3 in FIG. 5 is a CD (circular dichroism) spectrum of the sample 20 obtained by spectrum measurement, for example. Further, Spectrum 3 is shown as a schematic spectrum to make explanation of spectrum determination in the present embodiment easier. As shown in FIG. 5, the reference spectrum stored in the storage unit 26 and Spectrum 3, which is the CD spectrum of the sample 20, are compared to specify the sample 20 (identification of the sample 20 and confirmation of denaturation of the same).

First of all, the individual coincidence is calculated for each point of Spectrum 3 with respect to the reference spectrum. In FIG. 5, the individual coincidence at each point is as follows: 75% at Point A; 65% at Point B; and 97% at Point C. When three points of A to C are used to calculate (analyze) the individual coincidence of Spectrum 3 by a general method, 75% (Point A)+65% (Point B)+97% (Point C)/3 gives 78% as the individual coincidence of Spectrum 3. When the individual coincidence of 80% or more is regarded as coincidence, and less than 80% is regarded as non-coincidence, for example, Spectrum 3 is not coincident with the reference spectrum. However, a part important for spectrum determination (a part having a large effect on spectrum determination) and a part that is not (a part having a small effect on spectrum determination) exist in spectrum determination.

Hence, in the present embodiment, the weighting is set differently for each point of the reference spectrum, so that determination with high accuracy compared to conventional devices/methods becomes possible. Specifically, in FIG. 5, the weighting at Point A having low spectral reproducibility, is set to 0.4, and the weighting at Point B also having low spectral reproducibility is set to 0.6. The weighting at Point C, which is a point of high spectral reproducibility, is set to 1.0. When the individual coincidences of Points A to C and the respective differing weightings are used to calculate the coincidence of Spectrum 3, (75%×0.4)+(65%×0.6)+(97%× 1.0)/(0.4+0.6+1.0) gives 83% as the coincidence of Spectrum 3. When the individual coincidence of 80% or more is regarded as coincidence, and less than 80% is regarded as non-coincidence, for example, Spectrum 3 is coincident with the reference spectrum.

As stated above, the results differed between the determination result obtained by the conventional simple calculation (analysis) and the determination result obtained by calculating with the differing weighting for each point like the present embodiment. It can be said that an accurate identification of a spectrum becomes possible by focusing on the part important for spectrum determination and reflecting the differing weighting for each point to spectrum determination.

Further, the present embodiment is not limited to spectrum determination devices. Specification of a sample by good spectrum determination can be achieved by a spectrum determination method which performs the steps in order as described above. Specifically, reference measurement is performed for 5 to 20 times or more to measure a spectrum group at first. The spectrum group measured by reference measurement is used to prepare the reference spectrum having the average spectrum and differing weightings for each point as described above. Then, spectrum measurement is performed to detect the sample spectrum, and the individual coincidence with the sample spectrum is calculated for each point of the reference spectrum. The coincidence of the sample spectrum with the reference spectrum is calculated by the individual coincidence and the differing weighting. Thus, the spectrum determination method with good determination accuracy can be achieved.

Further, in spectrum determination, there are a region where dispersion is too large, and a region where dispersion is extremely small because a spectrum signal is not present. For example, in a CD spectrum of protein, noise tends to be large in a short-wavelength region, and such region is not suitable for comparison. Thus, the region for comparing the reference spectrum and the sample spectrum can be limited to a specific range of dispersion (eliminating the regions where dispersion is too large and extremely small) to improve determination accuracy.

In the present embodiment, determination of a CD spectrum by the circular dichroism measurement device is described. However, it is not limited to a spectrum measured by such measurement device, but can be used to a spectrum measured by other spectrum measurement devices. Further, such device and method for spectrum determination as described above can obtain highly accurate determination result when spectrum determination is performed by CD measurement to confirm extremely small phenomenon such as confirmation of denaturation in protein-derived biomedicines, for example.

Needless to say, the spectrum determination device in the present embodiment can be provided separately from the spectrum measurement device. For example, the spectrum determination device can determine whether the sample spectrum measured by the spectrum measurement device coincides with the reference spectrum or not. In this case, a spectrum determination device capable of spectrum determination by installing a program to a commercially available personal computer may be provided.

As described above, according to the spectrum determination device of the present invention, the spectrum determination device 10 comprises the storage unit 26 for storing the reference spectrum and the determination unit 28. The differing weighting is set for each point of the reference spectrum to calculate the individual coincidence of the sample spectrum with the reference spectrum for each point. Then, the coincidence of the sample spectrum is calculated by the individual coincidence and the differing weighting, so that the sample can be specified with high accuracy. For example, for each point of the reference spectrum, the weighting is set lightly to the part where dispersion of the spectrum group is large (a point where dispersion is large), and the weighting is set heavily to the part where dispersion of the spectrum group is small (a point where dispersion is small), so that the sample can be specified with good determination accuracy.

Further, according to the present invention, a spectrum measurement method with good determination accuracy can be achieved. The method comprises the steps of: setting the differing weighting for each point of the reference spectrum; detecting the sample spectrum by spectrum measurement; and calculating individual coincidence with the sample spectrum for each point of the reference spectrum. The coincidence of the sample spectrum with the reference spectrum is calculated by the individual coincidence and differing weighting for comparison.

DESCRIPTION OF REFERENCE NUMBERS

10 Spectrum determination device (determination device comprising a circular dichroism measurement device)
12 Light source
14 Spectrometer
16 Polarizer
18 PEM
20 Sample
22 Detector
24 Determination section
26 Storage unit
28 Determination unit

What is claimed is:

1. A spectrum determination device for comparing a reference spectrum prepared from a spectrum group that has been measured multiple times and a sample spectrum to determine whether the sample spectrum coincides with the reference spectrum or not, the spectrum determination device comprising:
    a storage unit for storing the reference spectrum, and a determination unit for comparing the reference spectrum and the sample spectrum to determine the sample from a comparison result,
    wherein the reference spectrum is set with a differing weighting for each point;
    the determination unit calculates an individual coincidence with the sample spectrum for each point of the reference spectrum, and calculates a coincidence of the sample spectrum with the reference spectrum by the calculated individual coincidence and the differing weighting to determine the sample.

2. The spectrum determination device according to claim 1, wherein a part where dispersion of the spectrum group is large is lightly weighted, and a part where dispersion of the spectrum group is small is heavily weighted in the reference spectrum.

3. The spectrum determination device according to claim 1, wherein the differing weighting for each point of the reference spectrum is calculated by a standard deviation of dispersion of the spectrum group.

4. The spectrum determination device according to claim 2, wherein the differing weighting for each point of the reference spectrum is calculated by a standard deviation of dispersion of the spectrum group.

5. The spectrum determination device according to claim 1, wherein the reference spectrum stored in the storage unit is a circular dichroism spectrum, and the determination unit is capable of confirming denaturation of protein by the circular dichroism spectrum.

6. The spectrum determination device according to claim 2, wherein the reference spectrum stored in the storage unit is a circular dichroism spectrum, and the determination unit is capable of confirming denaturation of protein by the circular dichroism spectrum.

7. The spectrum determination device according to claim 3, wherein the reference spectrum stored in the storage unit is a circular dichroism spectrum, and the determination unit is capable of confirming denaturation of protein by the circular dichroism spectrum.

8. The spectrum determination device according to claim 4, wherein the reference spectrum stored in the storage unit is a circular dichroism spectrum, and the determination unit is capable of confirming denaturation of protein by the circular dichroism spectrum.

9. A spectrum determination method for comparing a reference spectrum prepared from a spectrum group that has been measured multiple times and a sample spectrum to determine whether the sample spectrum coincides with the reference spectrum or not, the spectrum determination method comprising steps of:
   setting a differing weighting for each point of the reference spectrum;
   detecting the sample spectrum by spectrum measurement;
   calculating an individual coincidence with the sample spectrum for each point of the reference spectrum; and
   calculating a coincidence of the sample spectrum with the reference spectrum by the individual coincidence and the differing weighting to determine the sample.

10. The spectrum determination method according to claim 9, wherein a part where dispersion of the spectrum group is large is lightly weighted, and a part where dispersion of the spectrum group is small is heavily weighted in the reference spectrum.

11. The spectrum determination method according to claim 9, wherein the differing weighting for each point of the reference spectrum is calculated by a standard deviation of dispersion of the spectrum group.

12. The spectrum determination method according to claim 10, wherein the differing weighting for each point of the reference spectrum is calculated by a standard deviation of dispersion of the spectrum group.

13. The spectrum determination method according to claim 9, wherein the reference spectrum prepared from the spectrum group is a circular dichroism spectrum.

14. The spectrum determination method according to claim 10, wherein the reference spectrum prepared from the spectrum group is a circular dichroism spectrum.

15. The spectrum determination method according to claim 11, wherein the reference spectrum prepared from the spectrum group is a circular dichroism spectrum.

16. The spectrum determination method according to claim 12, wherein the reference spectrum prepared from the spectrum group is a circular dichroism spectrum.

17. The spectrum determination method according to claim 13, wherein denaturation of protein can be confirmed by the reference spectrum which is the circular dichroism spectrum.

18. The spectrum determination method according to claim 14, wherein denaturation of protein can be confirmed by the reference spectrum which is the circular dichroism spectrum.

19. The spectrum determination method according to claim 15, wherein denaturation of protein can be confirmed by the reference spectrum which is the circular dichroism spectrum.

20. The spectrum determination method according to claim 16, wherein denaturation of protein can be confirmed by the reference spectrum which is the circular dichroism spectrum.

21. A non-transitory computer-readable medium storing a computer-readable program for executing the determination unit for comparing the reference spectrum and the sample spectrum to determine whether the sample spectrum coincides with the reference spectrum or not from its comparison result, the computer-readable program that executes steps of:
   setting a differing weighting for each point of the reference spectrum prepared from a spectrum group that has been measured multiple times;
   calculating an individual coincidence with the sample spectrum for each point of the reference spectrum; and
   calculating a coincidence of the sample spectrum with the reference spectrum by the individual coincidence and the differing weighting to determine the sample.

* * * * *